(12) United States Patent
Chi

(10) Patent No.: US 6,613,014 B1
(45) Date of Patent: Sep. 2, 2003

(54) CATHETER HUB WITH DETACHABLE PUSH DEVICE

(75) Inventor: David Chi, Cerritos, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 275 days.

(21) Appl. No.: 09/590,946

(22) Filed: Jun. 9, 2000

(51) Int. Cl.[7] .............................................. A61M 31/00
(52) U.S. Cl. ................................................... 604/93.01
(58) Field of Search ............................... 604/93.01, 57, 604/84, 280, 528, 317; 128/760; 206/364

(56) References Cited

U.S. PATENT DOCUMENTS

| | | | |
|---|---|---|---|
| 4,829,999 A | | 5/1989 | Auth |
| 4,874,371 A | | 10/1989 | Comben et al. |
| 4,886,507 A | * | 12/1989 | Patton et al. ............... 604/284 |
| 4,944,740 A | | 7/1990 | Buchbinder et al. |
| 4,976,689 A | | 12/1990 | Buchbinder et al. |
| 5,106,054 A | * | 4/1992 | Mollenauer et al. ..... 251/149.1 |
| 5,125,895 A | | 6/1992 | Buchbinder et al. |
| 5,137,176 A | * | 8/1992 | Martineau et al. ....... 206/524.1 |
| 5,137,517 A | * | 8/1992 | Loney et al. ............. 24/115 M |
| D329,698 S | | 9/1992 | Loney et al. |
| 5,161,534 A | | 11/1992 | Berthiaume |
| 5,219,332 A | * | 6/1993 | Nelson et al. ............... 600/434 |
| 5,254,088 A | | 10/1993 | Lundquist et al. |
| 5,324,271 A | * | 6/1994 | Abiuso et al. ......... 604/167.03 |
| 5,330,434 A | | 7/1994 | McFarlane |
| 5,338,314 A | * | 8/1994 | Ryan .................... 604/167.06 |
| 5,391,172 A | | 2/1995 | Williams et al. |
| 5,423,331 A | | 6/1995 | Wysham |
| 5,599,305 A | * | 2/1997 | Hermann et al. ........... 604/200 |
| 5,820,600 A | * | 10/1998 | Carlson et al. .......... 251/149.2 |
| 5,830,183 A | | 11/1998 | Krieger |
| 5,843,031 A | | 12/1998 | Hermann et al. |
| 5,846,221 A | | 12/1998 | Snoke et al. |
| 5,851,189 A | * | 12/1998 | Forber ........................ 600/433 |
| 5,902,275 A | | 5/1999 | Dobkin |
| 5,911,710 A | * | 6/1999 | Barry et al. ........... 604/167.04 |
| 5,944,727 A | | 8/1999 | Ahari et al. |
| 6,027,460 A | * | 2/2000 | Shturman .................... 600/129 |
| 6,033,382 A | * | 3/2000 | Basta .......................... 604/104 |
| 6,050,958 A | * | 4/2000 | Dickinson et al. .......... 600/585 |
| 6,186,999 B1 | | 2/2001 | Chen |
| 6,190,360 B1 | | 2/2001 | Iancea et al. |
| 6,331,176 B1 | * | 12/2001 | Becker et al. ............... 604/533 |

FOREIGN PATENT DOCUMENTS

| | | |
|---|---|---|
| EP | 0 282 580 B1 | 9/1986 |

* cited by examiner

*Primary Examiner*—Daniel Robinson
(74) *Attorney, Agent, or Firm*—Fulwider Patton Lee Lee & Utecht, LLP

(57) ABSTRACT

A handle member for gripping a catheter shaft to facilitate advancement in a patient's body lumen. The handle member is configured to be releasably secured to the catheter shaft. Further, the handle is longitudinally displaceable along at least a length of the catheter shaft, so as to be slidably positional along the shaft. The handle member may be detachably connected to an adapter on the proximal end of the catheter shaft. Additionally, one embodiment of the handle member has internal grooves on the outer wall of the handle member, so that the user would have finger placement holds. The handle member may be made of a softer material than the catheter shaft, and have a tapered outer surface for comfort of the user.

25 Claims, 2 Drawing Sheets

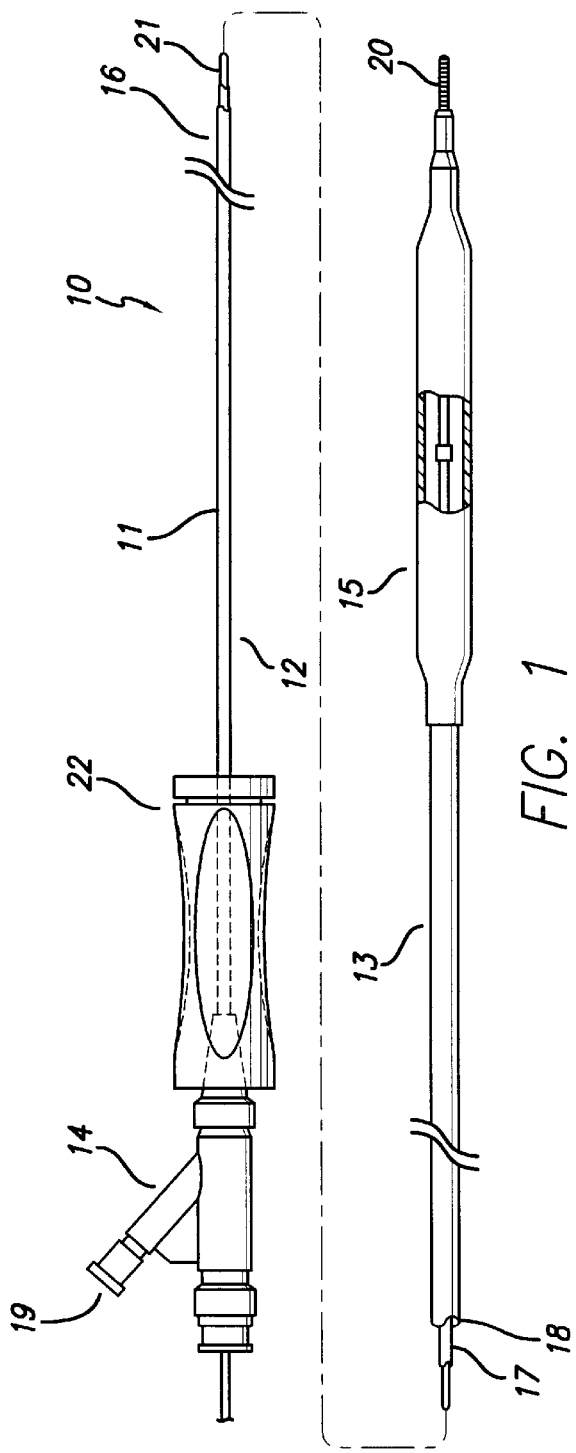
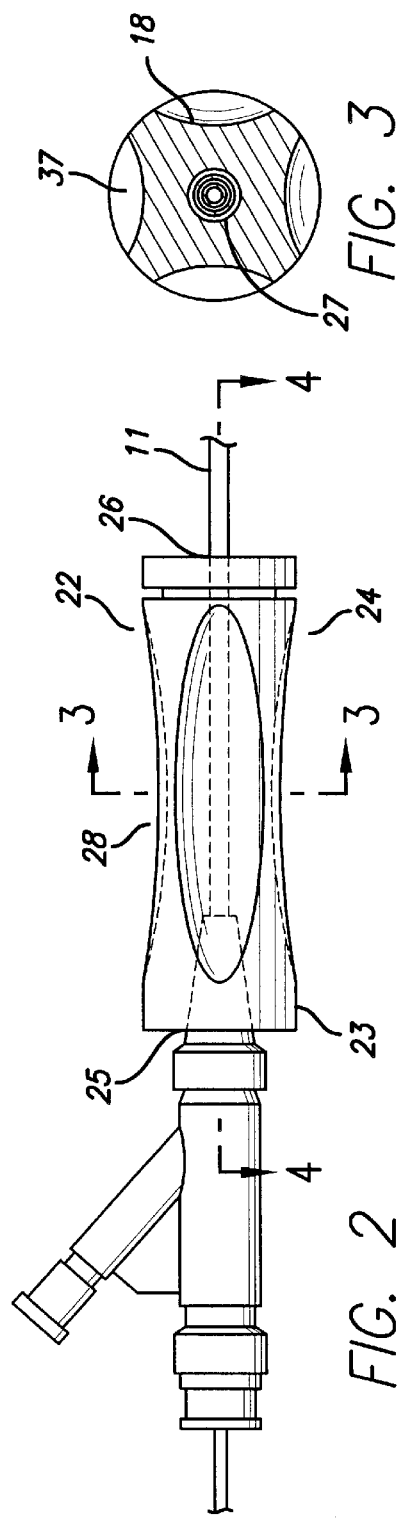

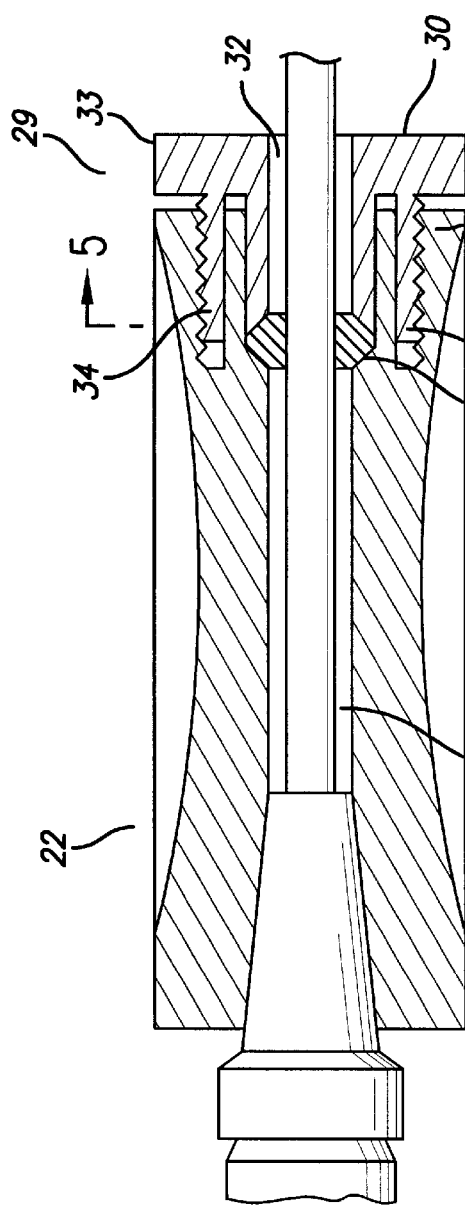
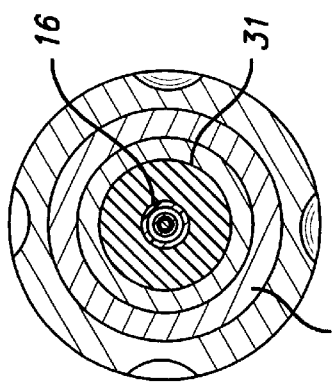
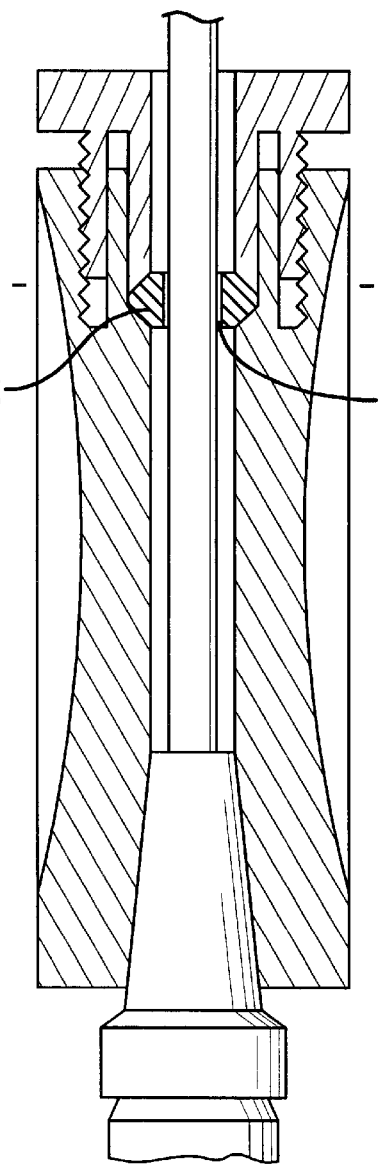
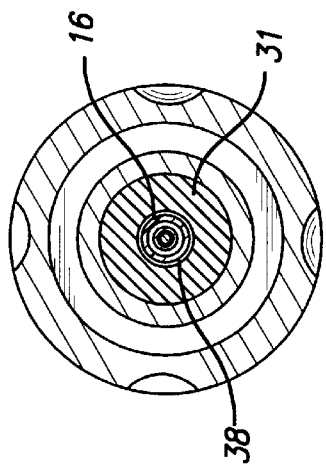

CATHETER HUB WITH DETACHABLE PUSH DEVICE

BACKGROUND OF THE INVENTION

This invention generally relates to intravascular catheters, such as balloon catheters used in percutaneous transluminal coronary angioplasty (PTCA) and stent delivery.

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery over a guidewire until the balloon on the catheter is disposed within the stenotic region of the patient's artery.

The balloon is inflated to open up the arterial passageway and increase the blood flow through the artery. Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed therefrom.

In a large number of angioplasty procedures, there may be a restenosis, i.e. reformation of the arterial plaque. To reduce the restenosis rate and to strengthen the dilated area, physicians now frequently implant an intravascular prosthesis called a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent is left in place within the artery at the site of the dilated lesion.

In both applications, the catheter must be advanced through the body to the heart. Control and advancement of catheters is difficult because of their construction. The body of conventional catheters is long and tubular. The user must frequently manipulate, or torque, the catheter shaft on the proximal end to facilitate advancement of the catheter with a desired orientation on the distal end. To provide the needed control over the movement of the catheter, it is necessary that these tubular catheters be made somewhat rigid. However, catheters must be flexible enough to navigate through the body lumen to arrive at the desired location within the body where the medical procedures will be performed. An overly rigid catheter shaft will not track, or follow, the guidewire. Therefore, reaching the desired location with the rigid catheter is more difficult. In addition, the catheter shaft is lubricious and smooth. A lubricious shaft is necessary to facilitate advancement within the body lumen. A user may have difficulty creating a sufficient grip on the catheter shaft.

Therefore, what has been needed is a device that improves torquability of the catheter without interfering with the tracking and advancing of the catheter. The present invention satisfies these and other needs.

SUMMARY OF THE INVENTION

The present invention is directed to a handle member for gripping a catheter shaft to facilitate advancement on a patient's body lumen. The handle member is configured to be releasably secured to the catheter shaft. Further, the handle is longitudinally displaceable along at least a length of the catheter shaft, so as to be slidably positional along the shaft. The handle member is comprised of a proximal end, a distal end, at least one lumen extending therethrough, and a connecting member.

The proximal end and the distal end of the handle member each have ports. The ports are completely surrounded by the handle member material. The catheter shaft passes through the proximal end port, advances through the lumen and passes through the distal end port. The handle member may be slidably positional on the catheter shaft. In such an embodiment, the connecting member in the handle member can be engaged to connect with the catheter shaft upon reaching a desired position. The connecting member frictionally engages the catheter shaft. The connection allows the handle member to secure to the catheter shaft, so the handle member will not move.

In one embodiment of the invention, the handle member is disposed about a catheter shaft having an adapter attached to the proximal end of the catheter shaft. The handle member is disposed about the catheter shaft at a location distal to the adapter. In yet another embodiment, the handle member is detachably connected to the adapter.

The handle member may have a connecting member of any type that would adequately grip the catheter shaft. Such connecting members include, but are not limited to clips, clamps, clasps, vises, locks and valves. Specifically, a rotational hemostatic valve is an adequate connecting member. A rotational hemostatic valve ("RHV") generally utilizes a three-piece assembly. First, the RHV has a sleeve. The interior of the sleeve had threads. For this invention, the sleeve may be the distal end of the handle member. The RHV also has a cap that extends partially within the sleeve. The cap has threads corresponding to the sleeve internal threads. The third piece is an O-ring, or other compressible member. The cap will compress the compressible member when it is turned within the sleeve. The compressible member then grips the catheter shaft, anchoring the RHV.

An important aspect of this invention is not only the additional control it would grant the user, but the added comfort the user would experience. This is especially true for long procedures. An embodiment of the invention has outer walls, and a taper between the proximal and distal ends and the center of the handle member on the outer wall. This embodiment allows for more comfortable prolonged gripping. Another embodiment includes a deformation of the outer walls in such a way as to enhance user comfort. A specific embodiment defines internal grooves on the outer wall of the handle member. A user may prefer to use such internal grooves as finger holds, allowing the user to have a secure hold on the handle member without an uncomfortable grip. The user is thereby able to work with more control for a long period of time.

Additionally, the handle may be manufactured from a material that is softer than the catheter shaft. Therefore, a wide variety of soft polymeric materials allow for a comfortable grip. Specifically, a thermoplastic rubber such as Santoprene® thermoplastic rubber from Advanced Elastomer Systems, a soft and sticky material, is a successful material. Alternatively, a polycarbonate may form the push device to provide support and strength, with a layer of Santoprene® added to provide a better grip.

BRIEF DESCRIPTION OF THE DRAWINGS

FIG. 1 is an elevational view of the catheter system embodying features of the invention, with a handle member attached to an adapter.

FIG. 2 is an elevational view of the proximal portion of the catheter system of FIG. 1, with the handle member attached to an adapter.

FIG. 3 is a transverse cross sectional view of the catheter system of FIG. 2 taken along the line 3—3.

FIG. 4 is a longitudinal cross sectional view of the catheter system of FIG. 2 taken along the line 4—4 with the connecting member engaged.

FIG. 5 is a transverse cross sectional view of the catheter system of FIG. 4 taken along the line 5—5.

FIG. 6 is a longitudinal cross sectional view of the catheter system of FIG. 2 taken along the line 4—4 with the connecting member disengaged.

FIG. 7 is a transverse cross sectional view of the catheter system of FIG. 6 taken along the line 7—7.

DETAILED DESCRIPTION OF THE INVENTION

As shown in FIG. 1, the catheter 10 embodying features of the invention generally includes a catheter shaft 11 having a proximal end 12, a distal end 13, an adapter 14, and a handle member 22 slidably disposed about and capable of being releasably secured to the catheter shaft 11 at a location distal to an adapter 14. In the embodiment shown in FIG. 1, the handle member 22 is detachably connected to the adapter 14.

As shown in detail in FIGS. 2–7, the handle member 22 has a proximal end 23 and a distal end 24. The proximal end 23 has a proximal port 25 for receiving the catheter shaft 11. The distal end 24 has a distal port 26 for receiving the catheter shaft 11. The handle member 22 has at least one lumen 27 between the proximal port 25 and the distal port 26, which receives the catheter shaft 11. The handle member 22 is about 1 to about 2 inches long. The lumen 27 defines an inner diameter. The inner diameter of the lumen 27 is generally no less than about 0.040 inches (1.016 millimeters).

The handle member 22 has an outer diameter. In one embodiment, the outer diameter is not constant. Specifically, the outer diameter is larger at the handle member proximal end 23 and distal end 24 than the outer diameter at any point between the proximal end 23 and distal end 24. The outer diameter will range from about 0.5 inches (12.7 millimeters) to about 2.0 inches (50.8 millimeters). In certain embodiments, the outer diameter tapers from a larger to a smaller transverse dimension from the proximal end 23 to the center 28 of the handle member 22, and from a smaller to a larger transverse dimension from the center 28 to the distal end 24.

The handle member preferably has a deformation on the outer surface to enhance comfort of the grip for the user. This deformation may be a texture on the outer surface, for example a sandpaper texture (not shown). The deformation may also include a design in the outer surface to conform to the user's hand (not shown). The deformation may also be a specific removal of material from the outer surface to enhance finger placement, such as a dimple or a slot (not shown). In one embodiment of the invention illustrated in FIG. 3, the handle member 22 may have internal grooves 37 in the sides. These grooves 37 will allow for comfortable finger placement during long procedures and a generally more ergonomic grip. Certain embodiments may have at least two internal grooves 37. Another embodiment may have the internal grooves 37 shaped as ovals. Specifically, these internal grooves 37 are configured to receive a physician's fingers. In such an embodiment, the circle created before forming the internal grooves 37 defines the outer diameter. The embodiment illustrated in FIG. 3 has four oval shaped grooves 37. However, any number of internal grooves would be adequate for this invention.

The handle member 22 has a connecting member 29 to connect the handle member 22 to the catheter shaft 11. The connecting member 29 may be, but is not limited to, any available clip, clamp, clasp, vise, lock or snap Specifically, the system used in a rotational hemostatic valve would be an adequate connecting member 29. In the embodiment shown in FIG. 4, the connecting member 29 consists of a cap 30 and a compressible ring 31 within a distal portion of the handle member lumen 27. In that embodiment, the connecting member 29 frictionally engages the catheter shaft 11 when secured thereto.

The cap 30 has a lumen 32 for receiving the catheter shaft 11. Similarly, the compressible ring 31 has a lumen 38 for receiving the catheter shaft 11. The cap 30 has a head 33 and a body 34. The body 34 extends within the handle member lumen 27. The body 34 has external threads 35 at least partially along the body's 34 longitudinal axis. The handle member 22 has internal threads 36, which compliment the external threads 35 on the body 34, on the distal end of the lumen 27. For the purposes of this patent, complimenting threads are threads that can receive each other. When the physician turns the head 33, the external threads 35 follow the internal threads 36 and rotate, moving the cap 30 toward the handle member proximal end 23.

The proximal movement will compress the compressible ring 31. The compressible ring 31 has a lumen 38, which disappears as the compressible ring 31 contacts the catheter shaft 11. The further the physician turns the head 33, the more proximal the body 34 will travel and the compressible ring 31 will compress to form a firm grip on the catheter shaft 11. FIG. 5 shows the connecting member 29 engaged to grip the catheter shaft 11. FIG. 6 shows the cap 30 open so the compressible ring 31 does not engage the catheter shaft 11. Compressible ring lumen 38 is clearly visible in FIG. 7.

Referring back to the embodiment illustrated in FIG. 1, the catheter 10 is an over-the-wire catheter. The catheter shaft 11 has an outer tubular member 17 and an inner tubular 16 disposed within the outer tubular member 17 and defining, with the outer tubular member 17, an annular inflation lumen 18. Inflation lumen 18 is in fluid communication with an inflatable balloon 15. Inflation fluid is introduced into the inflation port 19 on the adapter 14, travels through the inflation lumen 18, and inflates the balloon 15. The inner tubular member 16 has an inner lumen 21 extending therein, which is configured to slidably receive a guidewire 20 suitable for advancement through a patient's coronary arteries. The distal extremity of the balloon 15 is sealingly secured to the distal extremity of the inner tubular member 16, and the proximal extremity of the balloon 15 is sealingly secured to the distal extremity of the outer tubular member 17.

Although individual features of embodiments of the invention may be shown in some of the drawings and not in others, those skilled in the art will recognize that individual features of one embodiment of the invention can be combined with any or all the features of another embodiment.

What is claimed is:

1. A handle member for gripping a catheter shaft to facilitate advancement in a patient's body lumen comprising a body having a proximal end, a distal end, at least one lumen, an outer wall with internal grooves, and a connecting member, configured to be releasably secured to the catheter shaft and when released to be longitudinally displaceable along at least a length of the catheter shaft so as to be slidably positional along the shaft.

2. The handle member of claim 1, wherein the connecting member frictionally engages the catheter shaft when secured thereto.

3. The handle member of claim 1, wherein the connecting member is selected from the group consisting of clips, clamps, clasps, vises, locks, snaps, o-ring valves and rotational hemostatic valves.

4. The handle member of claim 1, wherein the connecting member comprises
   a) a cap having a head and a body with threads, the body extending within the handle member lumen;
   b) threads within the handle member lumen complimentary to the threads on the cap body; and
   c) a compressible member within the handle member lumen.

5. The handle member of claim 1, wherein the handle member lumen has an inner diameter of no less than 0.040 inches (1.016 millimeters).

6. The handle member of claim 1, wherein the handle member has an outer diameter of about 0.5 inches (12.7 millimeters) to about 2.0 inches (50.8 millimeters).

7. The handle member of claim 6, wherein the handle member body has a center section, and the handle member outer diameter at the center section is smaller than the outer diameter at the proximal end of the handle member body, and the handle member outer diameter at the center section is smaller than the outer diameter at the distal end of the handle member body.

8. The handle member of claim 7, having a proximal tapered portion between the center section and the proximal end and a distal tapered section between the center section and the distal end.

9. The handle member of claim 1, wherein the handle member body has a deformation configured to enhanced a user's grip.

10. The handle member of claim 1, wherein the grooves are configured in the shape of at least 2 ovals.

11. The handle member of claim 10 wherein the oval shapes are configured to receive a user's fingers.

12. The handle member of claim 1, wherein the handle member lumen has an inner diameter of no less than 0.040 inches (1.016 millimeters).

13. The handle member of claim 1, wherein the handle member has an outer diameter of about 0.5 inches (12.7 millimeters) to about 2.0 inches (50.8 millimeters).

14. The handle member of claim 13, wherein the handle member has a center section, and the handle member outer diameter at the center section is smaller than the outer diameter at the proximal end.

15. The handle member of claim 14, having a proximal tapered portion between the center section and the proximal end and a distal tapered section between the center section and the distal end.

16. A catheter, comprising;
   a catheter shaft having a proximal end, a distal end and at least one lumen; and
   a handle member for gripping a catheter shaft to facilitate advancement in a patient's body lumen comprising a body having a proximal end, a distal end, at least one lumen and a connecting member, configured to be releasably secured to the catheter shaft and when released to be longitudinally displaceable along at least a length of the catheter shaft so as to be slidably positional along the shaft, wherein the handle member is a softer material than the catheter shalt.

17. The catheter of claim 16, wherein the connecting member frictionally engages the catheter shaft when secured thereto.

18. The catheter of claim 16, further comprising an adapter attached to the catheter shaft proximal to the handle member.

19. The catheter of claim 16, wherein the handle member body has a deformation configured to enhanced a user's grip.

20. The catheter of claim 16, wherein the handle member body has an outer wall with internal grooves.

21. The catheter of claim 20, wherein the grooves are configured in the shape of at least 2 ovals.

22. The catheter of claim 21, wherein the oval shapes are configured to receive a user's fingers.

23. A catheter, comprising
   a shaft having a proximal end, a distal end, and at least one lumen; and
   a handle member on the catheter shalt for gripping the catheter shaft, comprising a body having a proximal end, a distal end, oval shaped grooves extending longitudinally along an outer surface of the handle member body, at least one lumen with a proximal portion of the catheter shall disposed therein, and a connecting member, configured to be releasably secured to the catheter shaft and when released to be longitudinally displaceable along at least a section of the catheter shaft so as to be slidably positional along the catheter shaft.

24. The catheter of claim 23, wherein the catheter is a balloon catheter having a balloon on a distal shaft section with an interior in fluid communication with the at least one lumen of the catheter shaft, and having a proximal adapter located proximal to the handle member and attached to the proximal end of the catheter shaft, the proximal adapter having an inflation port configured for connecting to a source of inflation fluid.

25. The catheter of claim 24, wherein the proximal adapter has threads on a distal portion, and the handle member has complimentary threads on the handle member proximal end.

* * * * *